US00PP14894P2

(12) United States Plant Patent
Benardella

(10) Patent No.: US PP14,894 P2
(45) Date of Patent: Jun. 8, 2004

(54) MINIATURE ROSE PLANT NAMED 'BENMINN'

(50) Latin Name: *Rosa hybrida minima*
Varietal Denomination: BENminn

(76) Inventor: Frank Benardella, 20 Stillhouse Rd., Englishtown, NJ (US) 07726

( * ) Notice: Subject to any disclaimer, the term of this patent is extended or adjusted under 35 U.S.C. 154(b) by 0 days.

(21) Appl. No.: 10/373,984

(22) Filed: Feb. 25, 2003

(51) Int. Cl.[7] ..... A01H 5/00

(52) U.S. Cl. ..... Plt./121
(58) Field of Search ..... Plt./121

*Primary Examiner*—Bruce R. Campell
*Assistant Examiner*—Susan B. McCormick

(57) ABSTRACT

'BENminn' is a new and distinct variety of miniature rose plant primarily identified by its vigorous, upright and spreading plant habit and it's medium pink flowers of hybrid tea form. There is little fade to the color of the flowers. Borne often in large sprays in such a manner that two or three sprays would make a notable bouquet. Flower stems within the sprays are a good length and can be cut individually to use for smaller bouquets or for exhibition.

1 Drawing Sheet

Genus/species: *Rosa hybrida 'minima'*.
Varietal denomination: 'BENminn'.

CROSS REFERENCE

The present invention bares some resemblance to 'BENmfig' (U.S. Plant patent application Ser. No. 09/783,455 filed Feb. 14, 2001, now abandoned) from the same breeding program with which it shares some of the same pollen parent, 'BENmagic' (U.S. Plant Pat. No. 8,603). Both 'BENmfig' and 'BENminn' are very vigorous miniature roses with pink blooms of hybrid tea form. Both are good as cut flowers with flowering stems of appropriate length. The primary differences between the two are that 'BENmfig' has a slightly more open plant habit, grows slightly taller and the blooms are usually varying shades of pink as opposed to the clear pink of this new invention.

BACKGROUND OF THE INVENTION

This present invention relates to a new and distinct variety of hardy, bush type plant of the miniature rose class and with exhibition form which is the primary objective of this breeding program. This new variety was created in a greenhouse in Englishtown, N.J. by crossing the following two rose plants:

The seed part is 'KORivo' for which no patent information was found.

The pollen parent is BENmagic (U.S. Plant Pat. No. 8,603).

This current invention is miniature rose plant with a vigorous, upright and spreading plant habit and medium pink flowers of hybrid tea form.

The seed parent, 'KORivo', is an ivory white, florabunda rose with hybrid tea form flowers, borne profusely on a bush with glossy foliage. Flower form and profusion of bloom of this new invention were probably derived from this seed parent.

'BENmagic', the pollen parent, is a miniature rose plant with red and white bicolor flowers, also with hybrid tea form, and with semi-glossy foliage. The only notable traits passed on to this present invention are it's miniature habit, hybrid tea form bloom and semi-glossy foliage.

Asexual reproduction by cuttings of this new variety in Rowley, Mass. have shown root development to initiate in 1 to 2 weeks on cuttings taken from new growth, depending on light and temperature, and that these rooted cuttings, grown on, show all distinguishing characteristics to continually come true to form.

BRIEF SUMMARY OF THE INVENTION

The present invention relates to a new and distinct variety of hardy dwarf bush type rose plant of the miniature class; the variety being primarily characterized—as to novelty—by it's large sprays of well formed, hybrid tea type, medium pink blooms.

The variety is further characterized by:

Flowers with exhibition potential

An abundance of flowers continually throughout the season

A slight rose fragrance

Vigorous, upright and spreading plant habit

Semi-glossy foliage

A plant which grows and blooms satisfactorily providing decoration and cut flowers in large containers both in the greenhouse and outdoors, as a garden perennial or specimen plant

BRIEF DESCRIPTION OF THE DRAWING

The accompanying drawing is a color photograph taken in February showing specimens of the buds, flowers and foliage of this new variety as grown under plastic in Essex County, Mass.

BOTANICAL DESCRIPTION OF THE PLANT

Following is a detailed description in outline form pertaining specifically to this new and distinct variety of miniature rose plant as between 4 and 5 years of age, growing indoors, under plastic in 8 inch standard nursery containers, in Essex County, Mass. All major color plate identifications made are referring to The Royal Horticultural Society Chart except where common terms of color definition are employed.

Genus/species: *Rosa hybrida* 'minima'.
Varietal denomination: 'BENminn'.
Commercial class: Miniature Rose.
Seed parent: 'KORivo'.
Pollen parent: 'BENmagic' (U.S. Plant Pat. No. 8,603).

FLOWERS

Blooming habit: Continuous.
Borne: In large sprays of 5 to 9 and sometimes singly.
Bud:

*Size.*—¾ of an inch in length and 15/32 inch in diameter at the widest point just before the sepals divide.

*Form.*—Ovate with acuminate tip.

*Sepals.*—Color — an olive green, between 146B and 146C, being the lighter shade in the center and toward attachment at base; inside surface lighter, near 146D. Size — inner two sepals about 1 inch long and outer three sepals about 1¼ inches long and both being ¼ inch wide near the base which is the widest part and excluding any foliation; extending ½ to ⅝ inch beyond the tip of the bud just before they start to divide. Surface texture — inside surface is pubescent; the outer surface of the two inner sepals is lightly pubescent and the outer surface of the three outer sepals is nearly glaborous but with an occasional hair and a rare stipate gland. Form — elongate, fused at receptacle and acute apex except 1 or 2 of the outer sepals having lanceolate tips; the three outermost sepals have 1 to 3 lanceolate foliar appendages along each margin. Characteristics — the two innermost sepals have pubescent margins and the three outermost sepals have many stipate glands along the margin and the appendages have stipate glands along their margins; rolling back with the petals and when flower is half open to a 45 degree angle with the peduncle and remaining thus until the petals start to drop and then rolling back almost to the stem where they remain attached to the receptacle.

*Peduncle.*—Length — 1½ to 1¾ inches in length. Aspect — straight. Strength — strong, erect. Color — yellow green, near 144A. Texture — smooth with several stipate glands randomly located.

*Receptacle.*—Diameter — about 5/16 inch. Color — near 144A. Texture — glaborous.

*Color.*—When sepals first divide — a medium pink, near 49B.

Bloom:

*Size.*—When fully expanded — 1¾ to 2¼ inches.

*Form.*—High centered until full open and then having a convex upper profile and a flat lower profile with petals becoming reflexed only at the edges.

*Petalage.*—16 to 22.

*Petaloids.*—0 to 5.

*Fragrance.*—slight.

*Persistence.*—Petals usually detach cleanly in 5 to 10 days, peduncle, recptacle and sepals remain and dry on plant.

*Lasting quality as cut flower.*—4 to 8 days.

Petals:

*Texture.*—Glaborous.

*Appearance.*—Inside and outside — satiny, with veins visible on the reverse fanning up and out from the base.

*Form.*—very broad fan shaped, rounded base and slightly emarginate at the point of attachment; margins entire except being emarginate or having a single minute serration at the outer apex; tight reflexing of edges.

*Length and width in inches.*—Outermost petals nearly as wide as they are long — 1¼ inches wide by 1 3/16 inch long.

*Arrangement.*—Arranged shingle-like.

*Color.*—During the first few days — between 65A and 52C at the center of the flower and near 65C on the edges of the outer petals; reverse of all petals is near 55C and near 4C at the base to about the inner ⅕ of the petal. When half blown — both inner and outer petals are near 55C and the edges are near 55D but are reflexed so as not to be seen and the petals appear to be all one tone of near 55C, and near 4C for the inner ¼ of the petal; the reverse of all petals is near 55D and near 158C at the base and coming about ¼ of the way up the petal. Color of the veins on the reverse of the petals is always the same as that of the base. Petals at point of attachment — near 5C. The bloom lightens somewhat as it ages becoming near 62C on the upper surfaces and near 158C coming ⅓ to ½ up the petals from the base; the reverse is near 162D and near 158D for about ⅓ of the way up from the base.

*General tonality.*—Medium pink.

Petaloids:

*Color.*—Same as that of the petals except there is apt to be a streak of the base color going up from the point of attachment to the tip.

*Size.*—Width — quite variable from ⅛ to 7/16 inch at the widest point length — 5/16 to ½ inch.

*Texture and appearance.*—Same as the petals except the veins are apt to be less noticeable.

REPRODUCTIVE ORGANS

Stamens, filaments and anthers:

*Arrangement.*—regularly arranged around styles.

*Quantity.*—Around 100.

*Filament.*—Length — varying 3/16 to 5/16 inch. General color — light yellow-green, near 1D.

*Anthers.*—Color — light yellow, near 16C.

Pollen:

*Color.*—A medium yellow-orange, near 21C, drying to a burnt orange, near 171B, as can be noted in the full open bloom in the accompanying drawing.

*Quantity.*—Ample.

Pistils, styles and stigmas:

*Quantity.*—About half as many as stamens.

*Styles.*—Thin; near even length, ⅜ inch. Color — translucent, near 66B from the red-purple group.

*Stigmas.*—Color — a very light pink, near 56B.

Hips: Does not set hips.

PLANT

Habit: upright, spreading and well branched.

Growth: vigorous and uniformly branched, maturing at a height between 28 and 36 inches and a width of 30 to 34 inches.

Length of flowering stem: averaging 6 to 8 inches in sprays and up to 13 inches when borne singly.

Foliage: pinnately compound usually with 5 leaflets, occasionally with 3 or 7.

*Size of mature leaf.*—4 to 5 inches from plant stem to tip when measured along the rachis; mature terminal leaflet — 1¾ to 2¼ inches from base to tip and 1⅛ to 1 5/16 inches wide at it's widest part.

*Quantity.*—Abundant.

*Leaflets.*—Shape — obtuse, acute apex and a cordate base. Color — anthocyanin coloration present on the young growth only. New foliage — medium green, upper surface, near 137C flushed lightly with near 183B; under surface near 146B, flushed with near 184B, veins are the same color as the under leaf surface. Older foliage — darker green, near 137A, on the upper surface and a medium green, between 147B and 146B, on the reverse with mid vein near 145A, secondary veins of near 147D, and tertiary venation near 147B appearing slightly darker than the under leaf surface. Appearance — upper surface, semi-glossy; underside, matte with veins protruding slightly. Texture — both surfaces are glaborous, under surface — lightly textured from veins and leathery. Edge — fine, uneven serration and with minute glands or stipate glands on and between many of the serrations.

*Petiole/rachis.*—Color on young leaf — upper side is a light yellow-green, near 144B and flushed with near 178B; the underside is near 146D and flushed very lightly with near 183C. Color on old leaf — upper side is a dark olive green, near 146B and margins of near 147A, underside near 144B. Texture — moderately smooth; Appearance — upper side is shallowy grooved with minute stipate glands on the edges of the grooves and occasional white hairs in the groove and numerous stipate gland and hairs at and around where leaflets are attached; the underside is smooth with an occasional prickle, randomly spaced stipate glands on the sides and an occasional hair, and near the base of the terminal leaflet and 2nd set of leaflets there are many stipate glands and a few hairs; at the basal leaflets there is no increase in the amount of stipate glands and there are no hairs present. Rachis — length varies from 2¾ to 3 inches on mature leaf.

*Leaflet petiolules.*—Color is the same as that of the leaf petiole on both surfaces except the anthocyanin coloration is more intense on the petiolules of the young leaflets; there are many stipate glands on the underside and also along the ridges of the upper side. Size — 1/32 to 2/32 of an inch long.

*Stipules.*—Very narrow, about 1/32 inch wide and about ⅝ inch in length and with edges reflexed. Margin — uneven serrulation with stipate glands on the tips of each serration, on the side of some serrations and with one or two in between the serrations.

Resistance: good resistance to downy and powdery mildews and insects; average resistance to blackspot; no rust observed.

Wood:

*New wood.*—Color — near 137B. Texture — smooth. Appearance — occasionally 1 to 3 hairs near the nodes with a few stipate glands located randomly.

*Old wood.*—Color — between 137C and 147B and having areas of and then becoming entirely covered with very slightly raised and corky textured surface and near 199B.

Thorns:

*Quantity.*—On main stalks — very few; on secondary stalks — very few for 1½ to 2 inches from base, then 3 to 4 per inch randomly arranged on the stem; on laterals, 3 to 4 per inch near the point of attachment and becoming one to none towards the tip.

*Form.*—An elliptical base tapering to a fine point, straight and angled slightly down, being 2/16 to 5/16 inch in length with the shorter ones being towards the base of the secondary stalks and laterals.

*Color when young.*—Near 182B from the greyed red group.

*Color when old.*—Between 174A and 174B from the greyed-orange group.

Prickles: 0 to 3 usually found on underside of the petiole/rachis only. Color — at their base they are the same color as the petiole/rachis and becoming near 182D at their tip Stipate glands: tips are near 183B.

Hairs: White hairs not visible to the naked eye were observed on different parts of the leaves and new wood.

Winter hardiness: Tested hardy in zones 4 through 9 with ample winter protection recommended zones 6 and colder.

It is claimed:

1. A new and distinct variety of hardy miniature rose plant is claimed, substantially as illustrated and described, characterized by a vigorous, upright and well branched plant bearing large sprays of medium pink blooms of hybrid tea form.

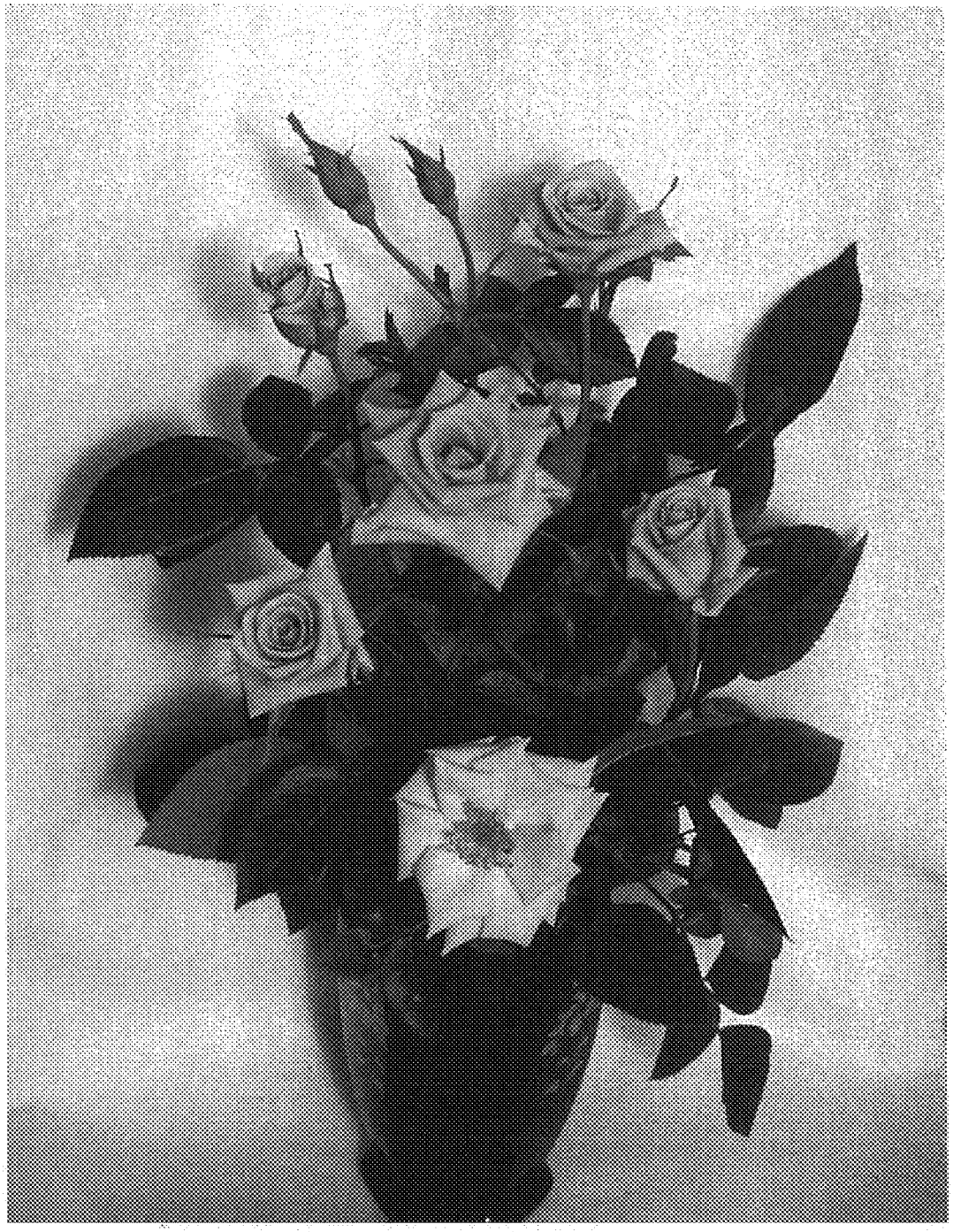

* * * * *